United States Patent
Weksel et al.

(10) Patent No.: US 11,439,772 B2
(45) Date of Patent: Sep. 13, 2022

(54) HOLLOW NEEDLE FOR ACCESS IN NON-LINEAR PATH

(71) Applicant: Jasperate, Inc., Lisle, IL (US)

(72) Inventors: David Weksel, Lisle, IL (US); Stephen Soloway, Vineland, NJ (US); Alyxandra Morgan Soloway, Vineland, NJ (US); Estella Yang Huang, Lisle, IL (US); Jacob Oliver Soloway, Vineland, NJ (US); Justine K. Weksel, Lisle, IL (US); Charles S. Brunner, North Reading, MA (US)

(73) Assignee: Jasperate, Inc., Lisle, IL (US)

( * ) Notice: Subject to any disclaimer, the term of this patent is extended or adjusted under 35 U.S.C. 154(b) by 729 days.

(21) Appl. No.: 15/909,548

(22) Filed: Mar. 1, 2018

(65) Prior Publication Data

US 2018/0264201 A1    Sep. 20, 2018

Related U.S. Application Data

(60) Provisional application No. 62/472,713, filed on Mar. 17, 2017.

(51) Int. Cl.
  *A61M 5/32* (2006.01)
  *A61B 17/34* (2006.01)
  *A61M 25/00* (2006.01)

(52) U.S. Cl.
  CPC ....... *A61M 5/3286* (2013.01); *A61B 17/3415* (2013.01); *A61M 5/329* (2013.01);
  (Continued)

(58) Field of Classification Search
  CPC .... A61M 5/158; A61M 5/3286; A61M 5/329; A61M 25/001; A61M 25/0043;
  (Continued)

(56) References Cited

U.S. PATENT DOCUMENTS

| 762,603 | A | * | 6/1904 | Witkowski | ............ | A61M 5/347 |
| | | | | | | 604/273 |
| 1,125,887 | A | * | 1/1915 | Schimmel | ............... | A61M 5/32 |
| | | | | | | 604/117 |

(Continued)

FOREIGN PATENT DOCUMENTS

| EP | 2907534 A1 | * | 8/2015 | ............ | A61M 5/158 |
| GB | 1400501 A | * | 7/1975 | ............... | A61M 5/32 |

*Primary Examiner* — Nathan R Price
*Assistant Examiner* — Mark A Igel
(74) *Attorney, Agent, or Firm* — Latimer LeVay Fyock LLC

(57) ABSTRACT

A hollow needle, for use in medical and other areas where thin hollow needles are used to inject or aspirate fluids and gases, is provided and comprises of a thin, rigid tube body that is open on both ends and throughout the length with one sharp end. The needle body is designed and can be manufactured with a curved shape and or other geometric features, can be drawn to a desired curvature with heat, or can be curved afterwards, to specific specifications depending on the application. The needle so configured advantageously allows the user to circumvent an obstacle and or obstacles that otherwise inhibit direct linear access to a point-of-interest by providing a device that can take the sharp point of a needle on an indirect path towards the desired therapy delivery point.

18 Claims, 4 Drawing Sheets

(52) U.S. Cl.
CPC .. *A61B 2017/3454* (2013.01); *A61M 25/0041* (2013.01); *A61M 25/0043* (2013.01)

(58) Field of Classification Search
CPC .. A61M 2005/3284; A61M 2005/3107; A61M 2005/3421; A61M 2005/341; A61M 2005/342; A61B 17/3415; A61B 2017/3454; A61B 17/3417; A61B 17/34; A61B 17/00
See application file for complete search history.

(56) References Cited

U.S. PATENT DOCUMENTS

| | | | | |
|---|---|---|---|---|
| 1,384,355 A * | 7/1921 | Smith | A61M 5/32 | 604/273 |
| 1,503,399 A * | 7/1924 | Webb | A61M 5/32 | 604/273 |
| 1,569,174 A * | 1/1926 | Crowther | A61M 5/34 | 285/114 |
| 1,882,213 A * | 10/1932 | Donovan | A61M 1/84 | 27/24.1 |
| 2,700,385 A * | 1/1955 | Ortiz | A61B 17/42 | 604/116 |
| 2,899,959 A * | 8/1959 | Ginsburg | A61M 5/32 | 604/174 |
| 3,097,647 A * | 7/1963 | Roehr | A61M 5/32 | 604/272 |
| 3,892,240 A * | 7/1975 | Park | A61B 17/06004 | 223/102 |
| 4,013,080 A * | 3/1977 | Froning | A61M 39/10 | 604/165.01 |
| 4,383,530 A * | 5/1983 | Bruno | A61M 5/3286 | 604/274 |
| 4,511,356 A * | 4/1985 | Froning | A61M 5/32 | 604/170.01 |
| 4,759,746 A * | 7/1988 | Straus | A61F 9/007 | 604/512 |
| 4,795,444 A * | 1/1989 | Hasegawa | A61M 3/00 | 604/218 |
| 4,889,529 A * | 12/1989 | Haindl | A61M 5/158 | 604/274 |
| 5,026,350 A * | 6/1991 | Tanaka | A61M 5/32 | 604/158 |
| 5,180,385 A * | 1/1993 | Sontag | A61B 17/062 | 606/224 |
| 5,199,445 A * | 4/1993 | Rubinfeld | A61F 9/00754 | 606/166 |
| 5,273,530 A * | 12/1993 | del Cerro | A61F 9/00736 | 604/521 |
| 5,290,267 A * | 3/1994 | Zimmermann | A61M 5/3286 | 604/274 |
| 5,336,239 A * | 8/1994 | Gimpelson | A61B 17/06066 | 606/223 |
| 5,431,649 A * | 7/1995 | Mulier | A61B 18/1477 | 606/41 |
| 5,456,675 A * | 10/1995 | Wolbring | A61M 5/158 | 604/537 |
| 5,643,292 A * | 7/1997 | Hart | A61B 17/0469 | 112/169 |
| 5,879,330 A * | 3/1999 | Bell | A61M 5/158 | 604/93.01 |
| 5,904,690 A * | 5/1999 | Middleman | A61B 17/29 | 606/113 |
| 5,927,562 A * | 7/1999 | Hammen | A61C 5/62 | 222/533 |
| 6,413,245 B1 * | 7/2002 | Yaacobi | A61F 9/0017 | 604/521 |
| 6,494,713 B1 * | 12/2002 | Pond | A61C 5/40 | 433/81 |
| 6,494,868 B2 * | 12/2002 | Amar | A61M 5/32 | 604/164.11 |
| 6,730,061 B1 * | 5/2004 | Cuschieri | A61M 5/3287 | 604/158 |
| 6,802,829 B2 * | 10/2004 | Buono | A61F 9/0017 | 604/218 |
| 7,601,707 B1 * | 10/2009 | Minks | A61K 9/0019 | 514/170 |
| 8,167,851 B2 * | 5/2012 | Sen | A61M 25/0631 | 604/263 |
| 8,353,876 B2 * | 1/2013 | Suwito | A61M 25/0097 | 604/174 |
| 8,409,167 B2 * | 4/2013 | Roschak | A61M 29/02 | 604/506 |
| 8,740,849 B1 * | 6/2014 | Fischell | A61M 25/0084 | 604/173 |
| 9,011,381 B2 * | 4/2015 | Yamada | A61M 25/06 | 604/164.01 |
| 2001/0037092 A1 * | 11/2001 | Amar | A61M 5/32 | 604/523 |
| 2002/0082584 A1 * | 6/2002 | Rosenman | A61M 25/0068 | 604/523 |
| 2003/0161824 A1 * | 8/2003 | Rackley | A61M 5/46 | 424/125 |
| 2006/0047250 A1 * | 3/2006 | Hickingbotham | A61M 5/1454 | 604/187 |
| 2006/0173440 A1 * | 8/2006 | Lamson | A61M 25/007 | 604/506 |
| 2006/0224118 A1 * | 10/2006 | Morris | A61M 25/0084 | 604/164.01 |
| 2007/0066944 A1 * | 3/2007 | Nyte | A61M 5/329 | 604/272 |
| 2007/0179455 A1 * | 8/2007 | Geliebter | A61M 5/329 | 604/272 |
| 2008/0269695 A1 * | 10/2008 | Perouse | A61M 5/158 | 604/240 |
| 2008/0312611 A1 * | 12/2008 | Racz | A61M 25/0009 | 604/272 |
| 2009/0182305 A1 * | 7/2009 | Tjelmeland | A61M 25/0606 | 604/506 |
| 2009/0192496 A1 * | 7/2009 | Suwito | A61M 25/0097 | 604/533 |
| 2010/0331794 A1 * | 12/2010 | Racz | A61B 17/3401 | 29/428 |
| 2013/0116556 A1 * | 5/2013 | Racz | A61M 5/158 | 600/431 |
| 2014/0121641 A1 * | 5/2014 | Fischell | A61M 25/0108 | 604/102.03 |
| 2014/0180222 A1 * | 6/2014 | Flaherty | A61M 25/0108 | 604/272 |
| 2014/0336456 A1 * | 11/2014 | Demers | A61B 10/04 | 600/137 |
| 2014/0358079 A1 * | 12/2014 | Fischell | A61B 5/6876 | 604/113 |
| 2015/0119674 A1 * | 4/2015 | Fischell | A61B 5/6852 | 606/41 |
| 2015/0119875 A1 * | 4/2015 | Fischell | A61B 18/1492 | 606/41 |
| 2015/0190587 A1 * | 7/2015 | Peh | A61M 39/0247 | 604/164.08 |
| 2015/0238170 A1 * | 8/2015 | Brunner | A61M 5/158 | 604/272 |
| 2015/0245863 A1 * | 9/2015 | Fischell | A61B 18/00 | 604/508 |
| 2020/0139055 A1 * | 5/2020 | Weksel | A61M 5/34 | |

* cited by examiner

FIG 1
Prior Art
FIG 2
Prior Art
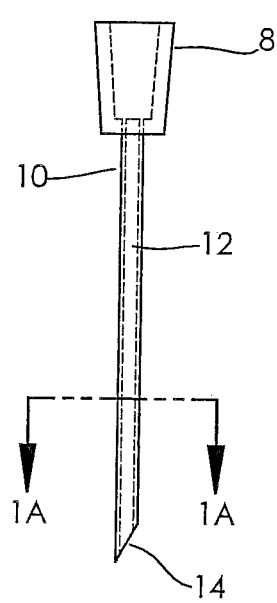
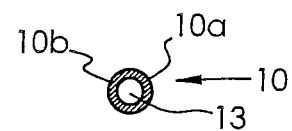
Fig 1A
Prior Art
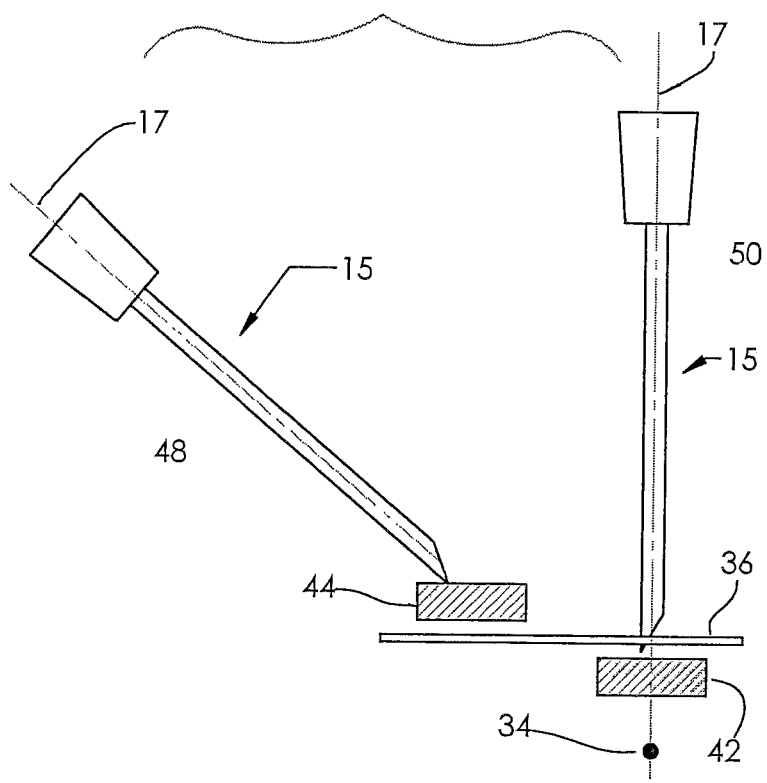

HOLLOW NEEDLE FOR ACCESS IN NON-LINEAR PATH

FIELD OF THE INVENTION

The present invention concerns needles used to provide access within a surface. More particularly the present invention concerns hollow needles used to penetrate skin or other body cavity or other surfaces to aspirate and or inject and or draw a liquid or other substances to and or from an area below the surface, defined as a point-of-interest; which point-of-interest is not necessarily in a straight line from the point of entry. The needles of the present invention could be classified as non-straight or having a bend therein.

BACKGROUND OF THE INVENTION

Hollow needles used in various medical procedures are also known as hypodermic needles. A needle of the type of the present invention is defined as a thin tube that can be inserted into a vein or body cavity to enable a number of different actions, including but not limited to administering medication, draining off fluid, or inserting a surgical instrument. These needles are traditionally straight, thin, hollow tubes with a sharpened tip at one end, known as the distal end and the sharpened tip is known as the bevel. Variations of needles traditionally refer to length and gauge, with gauge referring to the width of the needle. The width is often correlated to the thickness of the fluid or other material that can traverse the needle and or to the speed of aspirations and or injections. Commonly used with syringes, needles provide a means to penetrate human and or other animal tissue or synthetic materials to create a pathway to target the point-of-interest. The needle and syringe combination enables the user to aspirate and or inject medication and or to draw bodily fluids such as sanguineous or blood, purulent, serosanguinous, exudate, transudate, and or other fluids or materials. It should be noted that in some applications a desired action can be accomplished without the use of a syringe but by use of the needle alone or by integration of the needle with some other means of causing the action. A traditional hypodermic needle includes a straight, hollow needle tube and a leading sharp edge. As such, the use of needles is typically restricted to the direct line access through a surface, with little variation in the direction or path to which the action will occur. A straight needle is aimed from the surface so as to find its way, through a straight line to a targeted position. That is, once the target is chosen the user must, with prior art needles, aim and direct in a straight line for the target. Insertion of a needle into a body and then directing the needle to a location other than in a straight line is not possible with a straight needle most particularly due to obstructions or sensitive structures that are in the path, making the straight line needle difficult or dangerous.

The art of needles for use in medical procedures has advanced little beyond the earliest uses of puncturing the skin to arrive at a straight-line position for insertion or removal of fluids. Experimental uses of hypodermic needles for medical purposes were first performed in 17th century. However, due to poor results the technology was largely dormant until the 19th century when proper materials and construction techniques became available; uses also improved with the realization and implementation of sanitary conditions for medical procedures. Today, due to significant advances, hypodermic needles are a critical component of medical care procedures and research.

However, a significant drawback with the traditional hollow needle, as typically configured, continues to thwart their use in new and medically significant ways. Disadvantageously, in the use of traditional needles, there exists the problem that in the event of an obstruction either below or above the skin, the needle cannot easily access the point-of-interest below the skin or other tissue that requires the aspirating, injecting and/or drawing. For example, in the medical field, a traditional straight hypodermic needle may fail when a patient has metal and or other implants embedded under the skin and or when a tendon and or other sensitive tissue blocks straight access to a joint or another point-of-interest that needs to be aspired and/or injected and/or drawn. Another example is when a patient has issues of mobility or joints or tendons that are contracted, and the patient has no way of cooperating with positioning. The straight needle will not give appropriate access to the detriment of care of the patient.

Health care workers have been known to manually bend or otherwise manipulate the needle to enable access. However, surgical grade steel is typically not easy to manipulate and small tubes can be blocked or kinked by such manipulation such that they cannot work or work poorly. More typically, the health care worker attempts to manipulate the needle so as to angle the straight needle around the obstruction. Unfortunately, these practices usually require using a longer and perhaps wider needle, potentially causing damage to delicate arterial, venal or other structures. The costs to the health care worker and patient include the added time requirements while safety and maintaining manufacturing and structural integrity issues may arise. In addition, this can lead to inhibited flow through the needle and additional patient and health care worker trauma from the use of a larger needle.

The provision of needles having some curvature has been shown, in for example U.S. Pat. No. 5,290,267 to Zimmermann for "Hypodermic Needle," issued Mar. 1, 1994, where a cannula tube is bent laterally with a hook-shaped curved section is disclosed. However, Zimmerman's invention provides only for an advantage during piercing of natural and synthetic walls to avoid some damage to the walls. As shown in Zimmerman, the angle of curvature is slight with the extent of the curvature bringing the point of the needle back to the center line of the needle cylinder; the stated purpose being that during piercing of walls the cutting of plugs from the material, a typical result of the action of insertion of a hollow sharp, is avoided. There is no consideration in the disclosure of Zimmerman for accessing obstructed points-of-interest that requires aspiring and or injecting and or drawing.

In addition, non-straight needles are well known in suturing and dispensing applications. In the case of suturing, non-straight needles are typically used for cutting and supporting surgical procedures but, due to their very nature, fail to meet the needs of aspiring, injecting, or drawing. In the case of dispensing, non-straight needles are typically used to place a bead of material on a surface. For example, glue can be placed on a surface to assist with a manufacturing or assembly operation. However, dispensing cannot penetrate a surface to be used for aspiring, injecting, or drawing and cannot pass regulatory requirements for safety and efficacy.

It is therefore an object of the present invention to provide a device and means to access an indirect point-of-interest in a body where a straight-line approach is not possible. It is a further object of the present invention to provide a medical professional with alternative easier means to provide rapid and accurate health assistance in routine and emergency situations where obstructions would normally curtail the effectiveness of the use of hypodermic needles. Other objects and advantages of the present invention will become apparent as the description proceeds.

SUMMARY OF THE INVENTION

In accordance with the present invention, a hollow needle is provided comprising a cylindrical tube having an upper section defining a first opening and a sharpened point defining a second opening with a shaft therebetween. The tube defines a longitudinal axis therethrough and has a lumen extending from the upper section of the needle to the sharpened point—such that fluids or suspended solids or gases or other material capable of transport through the needle can pass through the needle. The shaft has a distal portion, which is curved relative to the longitudinal axis of the tube such that the distal end of the shaft and the sharpened point curve away from the axis of the tube. This curve then allows the needle to penetrate a surface, at a location, with the sharpened point and then be driven to a position non-linearly distal from the surface penetration location. In this way, the needle can be driven to the correct point when there is not a direct, linear, path from the surface to the point.

It will be seen that to be effective in reaching non-linearly placed targets, the shaft and point can be made to curve from between 5 degrees and 90 degrees from the axis of the tube in embodiments of the present invention. In the most common iteration of the present invention, the shaft and point are made to curve 45 degrees from the axis of the tube.

In embodiments of the present invention, the hollow needle can be made so that the shaft is further curved to give the needle a varied direction. That is, the shaft is curved first so that the curved portion is curved out from the axis of the tube, and then an additional curve can be created so that the needle can be directed in a direction generally lateral to the axis of the tube. It will be seen that to provide for the movement of material through the needle, the diameter of the lumen is made such that it is consistent throughout the length of the needle. The needle in the device of the present invention is made of steel, and more particularly surgical steel. It will be understood, however, that needles made in accordance with the teachings of the present invention can be made of any materials used by persons having skill in the art to make needles, including a variety of metals, alloys, plastics and such materials as carbon fiber and other; and that the variety of materials may assist in providing needles of various curvatures and nonlinear shapes without blocking the lumen.

In the creation of such needles it will be seen that the needle can be bent after manufacture using controlled bending techniques known to those having ordinary skill in the art that the needle can be cast with the curve or other nonlinear shape at its creation or can be drawn into a curve or nonlinear shape by heat applied processes during or after creation or can be fabricated from multiple pieces through welding or other known processes including the use of bending machines located in or near the point of usage of the device of the present invention.

Once created, the method of use of the hollow needle having a curved or nonlinear section will be easily understood as a very desirable manner of reaching a point-of-interest within a surface or barrier that is not in a direct linear direction from a location outside. The use will include the steps of placing the sharpened point of the needle upon a barrier or surface to be pierced then applying pressure to the opposite end of the needle at or near the syringe or connected device, if any, so as to cause the sharpened point of the needle to pierce the barrier or surface. The user will then apply appropriate force in the direction of the curve of the needle, and thereby push the sharpened point of the needle around any obstruction towards the point-of-interest so that the needle can be used to deliver fluids or other materials or aspirate fluids as needed. In one example of the use, the sharpened point is placed on a finger, having at least a tendon and a pulley, and the sharpened point of the needle is pushed between a pulley of the finger and a tendon of the finger to reach the point-of-interest.

The present invention consists of a hollow needle that's comprised of a thin, rigid tube that's open on both ends and throughout the length with one sharp end. The needle body is designed and manufactured with a curved shape and or other geometric features to specific specifications depending on the application.

A more detailed explanation of the invention is provided in the following description and claims and is illustrated in the accompanying drawings.

BRIEF DESCRIPTION OF THE DRAWINGS

A better understanding of the present invention may be obtained with reference to the following description in conjunction with the drawings in which:

FIG. 1 is a front elevational view of a hollow needle of the prior art.

FIG. 1A is a cross sectional view of the hollow needle of FIG. 1, taken along the line 1A-1A of FIG. 1.

FIG. 2 is a front elevational view of a prior art hollow needle, shown in two potential start positions towards endeavoring to access the point-of-interest.

DETAILED DESCRIPTION OF THE ILLUSTRATIVE EMBODIMENT

Figure 3:
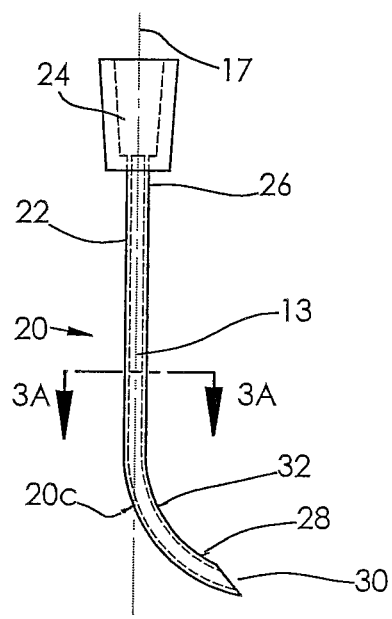
FIG. 3 is a front elevational view of one embodiment of the hollow needle of the present invention.
Figure 3A:
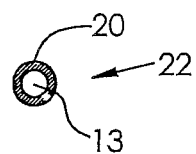
FIG. 3A is a cross sectional view of the hollow needle of FIG. 3, taken along the line 3A-3A of FIG. 3.

While the present invention is susceptible of embodiment in various forms, there is shown in the drawings a number of presently preferred embodiments that are discussed in greater detail hereafter. It should be understood that the present disclosure is to be considered as an exemplification of the present invention, and is not intended to limit the invention to the specific embodiments illustrated. It should be further understood that the title of this section of this application ("Detailed Description of the Illustrative Embodiment") relates to a requirement of the United States Patent Office, and should not be found to limit the subject matter disclosed herein.

Referring to FIGS. 1 and 1A, a needle or cannula 10 of the prior art is shown and includes a straight hollow needle tube 12 and a leading cutting edge 14. Needles 10 are typically made of three parts, the hub 8, the shaft 12 and the bevel 14. The hub 8 is at one end of the needle and is the part that attaches to a syringe or other medical apparatus. The shaft 12 is the long slender stem of the needle 10 that is beveled 14 at one end to form a point. The hollow bore of the needle is known as the lumen 13. Needle 10 is generally cylindrical and has comprises an inner generally cylindrical hollow section or lumen 13 therewithin, running the entire length of the needle 10. FIG. 1A, clearly shows the cross sectional view including the exterior surface 10a of the needle 10 and interior surface 10b of the hollow section 13 of the needle 10. It will be seen that the prior art needle is generally straight and when used as designed, provides access, to among other things, the interior of a body, by the puncturing of the skin or other barrier and thereby provides straight line access between an item connected to the needle and a body.

FIG. 2 illustrates a prior art hollow needle 15 shown in at least two positions, designated as positions 48 and 50 for ease of review. Position 48 shows a needle being driven at an angle towards a surface 44. It will be understood by persons having ordinary skill in the art that such a needle can be driven towards a surface at any angle relative to the surface, the illustrated position being only an example of such an angel. Position 50 shows a needle being driven at generally perpendicular to surface 36, which is of course one of the angels noted above, but is shown here to provide an example. Returning to FIG. 2, the needles in each of the two positions 48, 50 are being driven in an endeavor to access the point-of interest 34 by penetrating the skin 36. In position 48, an obstruction 44 is shown outside the skin 36 and blocks the straight access to point-of-interest 34. Similarly, in position 50, hollow needle 15 is inhibited from accessing the point-of-interest due to the embedded obstruction 42. Persons having ordinary skill in the art will recognize obstructions 42 and 44 can be of any type known, including natural occurring blocks such as tissue, organs, bone, tendons etc., as well as man made blockages such as implants, casts, bandages, etc.; further, the obstruction that blocks access externally can be a result of the position of the patient relative to the point-to-be accessed.

Figure 4:
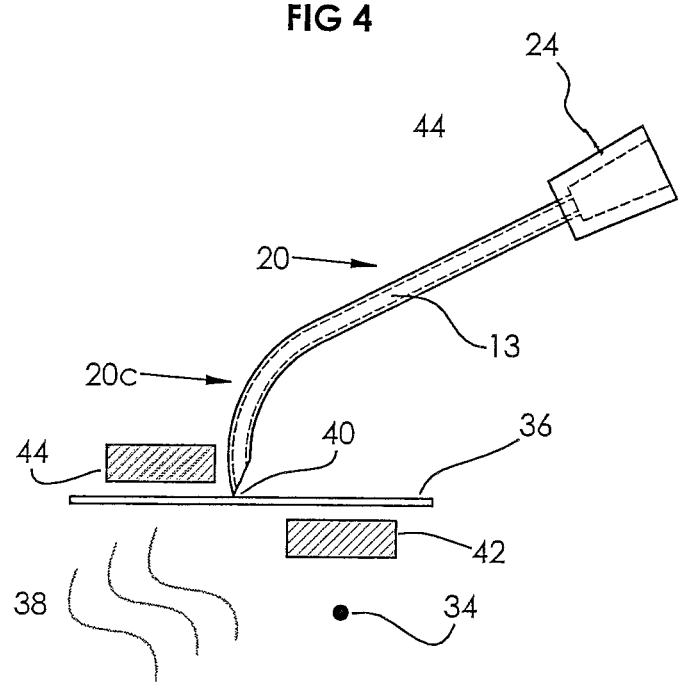
FIG. 4 is a front elevational view of one embodiment of the hollow needle of the present invention in the start position prior to accessing the point-of-interest under the skin.
Figure 5:
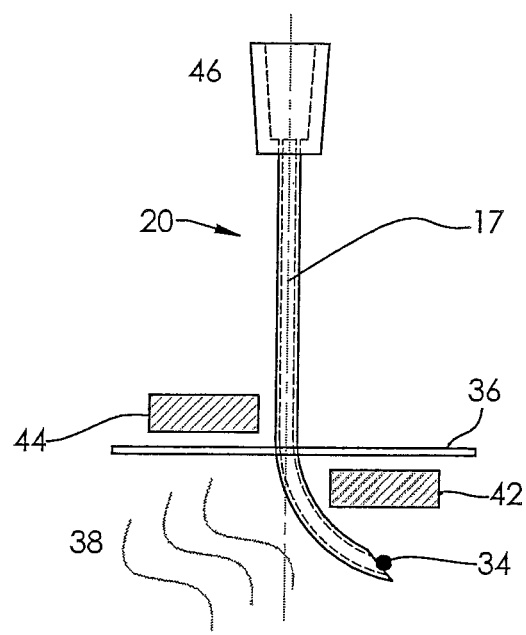
FIG. 5 is a front elevational view of one embodiment of the hollow needle of the present invention in the end position while accessing the point-of-interest under the skin by avoiding the obstructions.

Referring now to FIGS. 3, 4 and 5, a hollow needle 20 of the present invention is illustrated, comprising a thin, rigid tube body or shaft 22 receiving a syringe attachment mechanism (commonly a luer lock is used) 24 at end 26. Although this embodiment describes the use of a luer lock, other attachment mechanisms or hubs may be used for connection of the hollow needle 20 to a syringe or other medical device as known to persons having ordinary skill in the art. The most common connection of medical needles is a syringe, which typically comprises a cylindrical tube within which a plunger moves along its longitudinal axis 17 in a cavity designed to hold or receive liquids to inject or retract a substance from or into the syringe through the lumen 13 of needle 20 to or from a point-of-interest 34 under the skin 36. At the other end 28 of the body or shaft 22 there is a sharp tip 30 that is typically beveled, serrated, pronged, or otherwise configured to facilitate penetration of the skin 36 and other tissue and or substances 38 that's between the skin and the point-of-interest 34. Along the body or shaft 22 the hollow needle 20 of the present invention is provided with a curvature 32. The nature and dimensions of the curvature 32 is driven by the relative locations of the penetration point 40, the embedded obstruction 42, the outside obstruction 44, and the point-of-interest 34. It will be understood that the curvature 32 can have a variety of geometric features. Force and guidance is applied to the hollow needle at the starting position 40 to enable the hollow needle to penetrate the skin 36, to penetrate the other tissue and or substances 38, to circumvent the embedded obstruction 42, to circumvent the outside obstruction 44, to access the point-of-interest 34. All the time it will be understood that the direction of movement always follows the sharp tip 30 so as to cause the least harm to the tissue being penetrated. When tip 30 reaches the point-of-interest 34 the ending position 46 is achieved and the plunger on the syringe is engaged to commence aspiring and or injecting and or drawing. At the conclusion of the aspiring and or injecting and or drawing, the hollow needle 20 is retracted; pulled from the surface in a slow deliberate manner that allows the needle to retrace the insertion path on its way out, so as to cause as little harm as possible to the tissue. It will be understood by persons having ordinary skill in the art, that the use of a syringe to inject or remove fluids is an example of what can be done with the needle of the present invention and that any task which is facilitated by the use of a needle can be accomplishes with the present invention, including but not limited to injection, aspiration, catheterization, fluid insertion such as through intravenous drip and others, without departing from the novel scope of the present invention.

It will be seen that in at least one embodiment, the curvature of the needle is between 5 and 90 degrees relative to the center-line 17 of the needle and the degree of curvature is determined by the use of the needle and the needs of the body into which it is driven. In a preferred embodiment, the curvature of the needle is 45 degrees relative to the center-line 17 of the needle. It will be understood by persons having ordinary skill in the art that a bend between 0 degrees and 90 degrees, in any incremental angle, can be made without departing from the novel scope of the present invention. In the illustrative embodiment of the present invention, the curved portion 20c of the needle 20 occurs in the lower third of the shaft 22. It will be understood by persons having ordinary skill in the art that as needed, the curved portion 20c of a needle can be made at any point in the shaft 22 as required by the point-of-interest and the difficulty of approach. Persons having ordinary skill in the art will understand that the manufacture of the curve in a needle needs to be made in such a manner that the internal lumen is curved with the tube and that the lumen is not diminished significantly in diameter throughout the straight and curved sections of the needle. Such methods as drawing under heat or forcefully bending after packing an agent within the lumen and then using pipe-bending techniques to gradually curve the needle and then removing the packing to clear the lumen prior to use are but two of the many techniques that can be used to bend the needle of the present invention. Additionally the needle can be cast to the desired curve or can be heated until the meal is pliable and then bent are among the variety of ways that needles of the present invention can be formed with a curve.

Figure 3B:
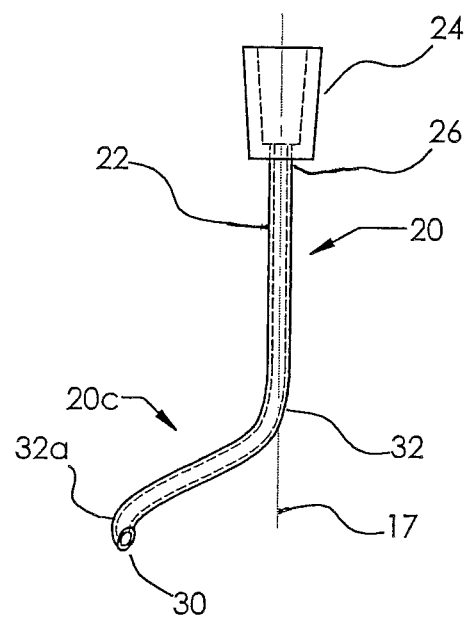
FIG. 3B is a front elevational view of another embodiment of the hollow needle of the present invention.
Figure 3C:
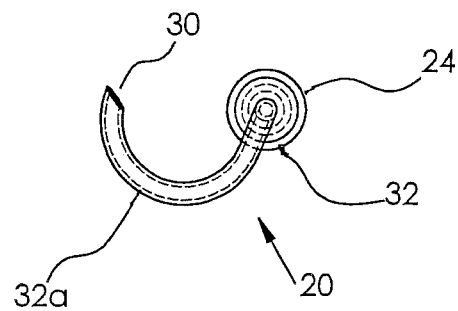
FIG. 3C is a bottom plan view of the needle of FIG. 3B.

Furthermore, a needle can be curved in a first direction and then as needed curved again, with more than one bend and in more than one direction. Such is shown in FIGS. 3B and 3C, where in addition to the curve 32 shown in FIG. 3, the needle is then curved again 32a distally from the curve 32, so that its point 30, as shown in FIG. 3B, is turned generally so that the end can be seen coming out of the page. While multiple curves would provide a more specialized path into a body, it will be understood by persons having ordinary skill in the art that specialized planned curved needles can be made in accordance with the teachings of the present invention to provide access to points-of-interest that are otherwise difficult to reach without departing from the teachings of the present invention.

One simple example, to show the improved results of using the present invention, is in the treatment of stenosing tenosynovitis, commonly known as trigger finger. As is known, the tendons that bend the fingers glide easily with the help of the annular ligaments or pulleys. Annular ligaments are fibrous sheaths that are thick and strong as required by the repetitive use that such a system by nature necessitates. Trigger finger occurs when the pulley becomes too thick, such as through swelling due to repetitive use injury, so that the tendon cannot glide easily through the pulley; this often manifests itself in a finger that is locked in place, in a "trigger-like" shape. Treatments of trigger finger include surgery, to open a section of the thick and fibrous pulley so as to allow the easier passage of the tendon therein and injection of a steroid to reduce the swelling. Oftentimes a doctor will first choose to provide an injection of a steroid between the tendon and pulley to reduce the swelling of the tendon and allow the tendon to glide through the pulley before considering surgery. In conventional treatment, a doctor will use a straight needle to inject into the finger, in a generally perpendicular motion relative to the finger, through the pulley and tendon and often to the bone. The patient will then wiggle the finger to allow the doctor to retract the needle; stopping the retraction when the syringe attached to the needle no longer wiggles with the finger. This is an indication that the needle is no longer in the tendon, such that the doctor can inject the medicine in the space between the tendon and pulley.

This technique is problematic in that damage is done to the pulley and tendon by being pierced with the needle and the patient is subjected to pain. A better technique would be to use the same needle to pierce the finger horizontally and drive the needle between the pulley and tendon; however, a straight needle will not work for this, due to the angles that the needle will need to take, as a result of the compactness of the tendon and pulley system.

We have discovered that the needle of the present invention, which as described above, can pierce the skin at one location and as a result of its configuration, be driven around the impediment to provide an appropriate dose of medicament to the exact location of the problem. Such an action can provide relief with a single treatment and not damage the pulley or tendon. The bend in the needle of the present invention provides an appropriate angle to pierce the skin and drive, generally horizontally, between the tendon and pulley and there deliver the medicine where needed. Little or no damage is then done to the pulley or tendon, and the patient has less discomfort as a result; treatment is completed more quickly and is more effective.

In the treatment of trigger finger it will be understood that a finger so affected is often caused, by the condition, to be bent so that the finger itself is a barrier to an injection between the pulley and the tendon. The bent condition, as is known to persons having medical experience, typically results because the swollen or enlarged part of the tendon is trapped within the thick and fibrous pulley such that a needle cannot reach the location of the swelling, both because of the position of the finger (bent back over the palm of the hand) and because the point of interest is within the pulley.

In the use of the injection, it will be understood that because of the position of the finger, bent above the point of interest, and the pulley, which is thick and fibrous, each comprise a blockage of the space between the pulley and the tendon. For this reason, it is often the case that the space cannot be reached using the conventional treatment protocols noted above, resulting in the need for more than one treatment, causing more damage to the pulley and the tendon in an effort to provide sufficient medicament to arrive at the desired result. When the space cannot be reached, treatment may require surgery with all of the attendant issues and problems of surgery.

Although an illustrative embodiment of the invention has been shown and described, it is to be understood that various modifications and substitutions may be made by those skilled in the art without departing from the novel spirit and scope of the invention.

What is claimed is:

1. A hollow hypodermic needle, solely for use in the deposit or collection of fluids from a body, the hollow-needle comprising:
   a generally rigid tube, having a generally circular cross section, comprising a first segment defining a first opening and a second segment characterized as having a portion of the generally rigid tube cutaway, at a distal end, to form a profile wherein a sharpened point and a generally oval opening are created, with a hollow shaft therebetween;
   the generally rigid tube having at least one lumen extending from the first segment to the sharpened point;
   a hub, substantially inseparably affixed at a hub distal end to the proximal end of the generally rigid tube, and having a hub proximal end configured to create a generally liquid and gas tight attachment interface to a fluid delivery or collection device;
   the hub defining at least one lumen extension therewithin and in fluid communication with the at least one lumen of the generally rigid tube, providing a continuous fluidic path, from the hub through the proximal end of the generally rigid tube and to the sharpened point of the hollow hypodermic needle;
   the fluid delivery or collection device having one or more positions thereon to allow a first motive force, to push fluid into and through the hypodermic needle or to pull fluid out of the body through the hypodermic needle, to be applied; and,
   the generally rigid tube having a proximal portion comprising a straight segment of shaft defining, with the hub, a hub-shaft longitudinal axis, and a distal portion which is curved relative to the hub-shaft longitudinal axis, such that the curved distal end of the shaft and the sharpened point are curved away from the hub-shaft longitudinal axis, the generally oval opening opens to the inside of the curve; and
   wherein upon the application of a second motive force, the sharpened point of the hollow needle can penetrate a surface, at a desired location, followed by the generally rigid tube, the sharpened point and tube then being forced through a non-linear path from the surface penetration point around an obstruction and to a desired point in the body for deposit or collection of fluids or both.

2. The hollow needle of claim 1, wherein the shaft and point curve between 5 degrees and 90 degrees away from the hub-shaft longitudinal axis.

3. The hollow needle of claim 1, wherein the shaft and point curve 45 degrees away from the hub-shaft longitudinal axis.

4. The hollow needle of claim 1, wherein the distal end of the shaft is further curved to give the distal end of the needle a compound curvature in a varied direction.

5. The hollow needle of claim 1, wherein a diameter of the at least one lumen is consistent throughout a length of the needle.

6. The hollow needle of claim 1, wherein the needle is made of steel.

7. The hollow needle of claim 1, wherein the needle is cast with the curve.

8. The hollow needle of claim 1, wherein the needle is heated and drawn to a desired curvature.

9. The hollow needle of claim 1, wherein the needle is bent further after primary manufacture.

10. The hollow needle of claim 1, wherein the needle is made of a material allowing the needle to be bent further, and retain the new bend, after manufacture and just prior to penetration.

11. The hollow needle of claim 10, wherein such bending is done using methods and devices that can cause a desired bend while maintaining the structural integrity of the needle including the lumen passage.

12. The method of use of a partially curved hypodermic needle having a hub connected to a proximal end, the curve of the hypodermic needle occurring at manufacture and curved specifically in such a way as to maintain an open lumen therewithin, having both a curved section and a sharpened point at a distal end of the hypodermic needle and having a straight section at the proximal end, the sharpened point being curved away from a longitudinal axis of the straight section of the partially curved hypodermic needle and having a generally oval opening adjacent thereto, the opening placed on the concave part of the curve of the hypodermic needle, to reach a point of interest within a surface or barrier solely to deposit or collect fluid and gas, including the steps of:
  placing the sharpened point of the hypodermic needle upon the barrier or surface to be pierced;
  applying force to the proximal end of the hypodermic needle to cause the sharpened point to pierce the barrier or surface and
  pushing the sharpened point and attendant shaft around an obstacle and towards the point-of-interest to deposit or collect fluid and gas, the movement of the hypodermic needle being limited by the hub, affixed to the proximal end of the hypodermic needle, striking the barrier or surface pierced.

13. The method of use of claim 12, wherein the sharpened point is placed on a finger, having at least a tendon and a pulley, and the sharpened point of the needle is pushed between the pulley of the finger and the at least one tendon of the finger to reach the point-of-interest.

14. The hollow hypodermic needle of claim 1, wherein the attachment mechanism is a Luer fitting.

15. The hollow hypodermic needle of claim 1, wherein the curve of the distal portion of the generally rigid tube defines a center of curvature defining an inner concave curve and an outer convex curve, the sharpened point at the distal and of the tube being located substantially on the outer convex curve of the generally rigid tube, the generally oval opening being located on the inner concave curve of the generally rigid tube.

16. A hollow hypodermic needle, solely for the deposit or collection of fluids from a body, the hollow-needle comprising:
  a generally rigid tube, having a generally circular cross section, comprising a first segment defining a first circular opening, and a second segment having a sharpened point defining a second opening, with a hollow shaft therebetween;
  the generally rigid tube having at least one lumen extending from the first segment to the sharpened point;
  a hub, substantially inseparably affixed at a hub distal end to a proximal end of the generally rigid tube, and having a hub proximal end configured to create a liquid and gas tight attachment interface to a fluid delivery device;
  the hub defining at least one lumen extension therewithin and in fluid communication with the at least one lumen of the generally rigid tube, providing a continuous fluidic path from the hub through the proximal end of the hollow hypodermic needle to the sharpened point of the hollow hypodermic needle;
  the fluid delivery or collection device having one or more positions thereon to allow a first motive force, to push fluid into and through the hypodermic needle or to pull fluid out of the body through the hypodermic needle, to be applied; and,
  the generally rigid tube having a proximal portion comprising a straight segment of shaft defining, with the hub, a hub-shaft longitudinal axis, the generally-rigid tube having a central portion which is multiply-curved, wherein, a first curve, relative to the hub-shaft longitudinal axis occurs such that a proximal end of the central portion of the shaft curves away from the hub-shaft longitudinal axis about a second axis, generally perpendicular to the hub-shaft longitudinal axis, and a second curve occurs, relative to the second axis, such that a distal section of the central portion is curved relative to a third axis that is offset to the hub-shaft longitudinal axis, to allow the sharpened point of the hollow needle to penetrate a surface, at a location, followed by the tube, the sharpened point and tube then being forced through a non-linear path from the surface penetration point around one or more obstructions and to a desired place in the body for deposit or collection of fluids or both.

17. The hollow hypodermic needle of claim 16, wherein the tube is further curved so that the third axis is generally perpendicular to the hub-shaft longitudinal axis.

18. The hollow hypodermic needle of claim 16, wherein the tube is further curved so that the third axis is generally parallel to the hub-shaft longitudinal axis.

* * * * *